United States Patent [19]

Jones et al.

[11] Patent Number: 4,547,607

[45] Date of Patent: Oct. 15, 1985

[54] METHANE CONVERSION PROCESS

[75] Inventors: C. Andrew Jones, Newtown Square; John J. Leonard, Springfield; John A. Sofranko, Malvern, all of Pa.

[73] Assignee: Atlantic Richfield Company, Los Angeles, Calif.

[21] Appl. No.: 600,878

[22] Filed: Apr. 16, 1984

Related U.S. Application Data

[63] Continuation-in-part of Ser. No. 522,925, Aug. 12, 1983, Pat. No. 4,443,649, Ser. No. 522,944, Aug. 12, 1983, Pat. No. 4,444,984, Ser. No. 522,942, Aug. 12, 1983, Pat. No. 4,443,648, Ser. No. 522,905, Aug. 12, 1983, Pat. No. 4,443,645, Ser. No. 522,877, Aug. 12, 1983, Pat. No. 4,443,647, Ser. No. 522,876, Aug. 12, 1983, Pat. No. 4,443,644, Ser. No. 522,906, Aug. 12, 1983, Pat. No. 4,443,646, Ser. No. 522,935, Aug. 12, 1983, , and Ser. No. 522,938, Aug. 12, 1983, , which is a continuation-in-part of Ser. No. 412,650, Aug. 30, 1982, abandoned, said Ser. No. 522,925, is a continuation-in-part of Ser. No. 412,667, Aug. 30, 1982, abandoned, said Ser. No. 522,944, is a continuation-in-part of Ser. No. 412,655, Aug. 30, 1982, abandoned, said Ser. No. 522,942, is a continuation-in-part of Ser. No. 412,662, Aug. 30, 1982, abandoned, said Ser. No. 522,905, is a continuation-in-part of Ser. No. 412,663, Aug. 30, 1982, abandoned, said Ser. No. 522,877, is a continuation-in-part of Ser. No. 412,664, Aug. 30, 1982, abandoned, said Ser. No. 522,876, is a continuation-in-part of Ser. No. 412,665, Aug. 30, 1982, abandoned, said Ser. No. 522,906, is a continuation-in-part of Ser. No. 412,666, Aug. 30, 1982, abandoned, said Ser. No. 522,935, is a continuation-in-part of Ser. No. 412,649, Aug. 30, 1982, abandoned.

[51] Int. Cl.$^4$ .............................................. C07C 2/00
[52] U.S. Cl. ................................. 585/500; 585/400; 585/417; 585/541; 585/654; 585/658; 585/700; 585/943
[58] Field of Search .............. 585/500, 400, 417, 541, 585/658, 654, 661, 700, 943

[56] References Cited

U.S. PATENT DOCUMENTS

| | | | |
|---|---|---|---|
| 3,845,156 | 10/1974 | Farha | 585/661 |
| 4,172,810 | 10/1979 | Mitchell, III et al. | 585/500 |
| 4,310,717 | 1/1982 | Eastman et al. | 585/661 |
| 4,368,346 | 1/1983 | Eastman | 585/658 |
| 4,443,649 | 4/1984 | Jones et al. | 585/500 |

OTHER PUBLICATIONS

Fang et al., "Catalytic Pyrolysis of Methane", J. of Chinese Chemical Society, 29, 265–273 (1981).

Primary Examiner—William R. Dixon, Jr.
Assistant Examiner—Cynthia A. Prezlock
Attorney, Agent, or Firm—Craig E. Larson

[57] ABSTRACT

A method is disclosed for converting methane to higher hydrocarbon product by contacting the methane with a solid which comprises a reducible metal oxide which when contacted with methane at a temperature within the range of about 500° to 1000° C. is reduced and produces higher hydrocarbon products and water, the improvement comprising recycling $C_{2+}$ alkanes recovered during subsequent processing of the effluent produced by the contacting to the contacting step.

8 Claims, No Drawings

METHANE CONVERSION PROCESS

CROSS REFERENCES TO RELATED APPLICATIONS

This application is a continuation-in-part of the following U.S. patent applications: (1) application Ser. No. 522,925 filed Aug. 12, 1983, now U.S. Pat. No. 4,443,649, which in turn is a continuation-in-part of application Ser. No. 412,667 filed Aug. 30, 1982, now abandoned; (2) application Ser. No. 522,944 filed Aug. 12, 1983, now U.S. Pat. No. 4,444,984, which in turn is a continuation-in-part of application Ser. No. 412,655 filed Aug. 30, 1982, now abandoned; (3) application Ser. No. 522,942 filed Aug. 12, 1983, now U.S. Pat. No. 4,443,648 which in turn is a continuation-in-part of application Ser. No. 412,662 filed Aug. 30, 1982, now abandoned; (4) application Ser. No. 522,905 filed Aug. 12, 1983, now U.S. Pat. No. 4,443,645 which in turn is a continuation-in-part of application Ser. No. 412,663 filed Aug. 30, 1982, now abandoned; (5) application Ser. No. 522,877 filed Aug. 12, 1983, now U.S. Pat. No. 4,443,647 which in turn is a continuation-in-part of application Ser. No. 412,664 filed Aug. 30, 1982, now abandoned; (6) application Ser. No. 522,876 filed Aug. 12, 1983, now U.S. Pat. No. 4,443,644 which in turn is a continuation-in-part of application Ser. No. 412,665 filed Aug. 30, 1982, now abandoned; (7) application Ser. No. 522,906 filed Aug. 12, 1983, now U.S. Pat. No. 4,443,646 which in turn is a continuation-in-part of application Ser. No. 412,666 filed Aug. 30, 1982, now abandoned; (8) application Ser. No. 522,935 filed Aug. 12, 1983, which in turn is a continuation-in-part of application Ser. No. 412,649 filed Aug. 30, 1982, now abandoned; and (9) application Ser. No. 522,938 filed Aug. 12, 1983, which in turn is a continuation-in-part of application Ser. No. 412,650 filed Aug. 30, 1982, now abandoned. The entire content of these applications is incorporated herein by reference.

BACKGROUND OF THE INVENTION

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. Oxides of manganese, tin, indium, germanium, lead, antimony and bismuth are particularly useful. See commonly-assigned U.S. Pat. Nos. 4,443,649; 4,444,984; 4,443,648; 4,443,645; 4,443,647; 4,443,644 and 4,443,646 all filed Aug. 12, 1983.

Commonly-assigned U.S. patent application Ser. No. 522,935, filed Aug. 12, 1983, discloses and claims a process which comprises contacting methane with an oxidative synthesizing agent under elevated pressure (2–100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—methane contact zone and an oxygen contact zone.

Commonly-assigned U.S. patent application Ser. No. 522,937, filed Aug. 12, 1983, discloses and claims a process for the conversion of methane to higher hydrocarbons which comprises contacting methane with an oxidative synthesizing agent containing a promoting amount of alkali metal and/or compounds thereof.

Commonly-assigned U.S. patent application Ser. No. 522,936 filed Aug. 12, 1983 discloses and claims a process for the conversion of methane to higher hydrocarbons which comprises contacting methane with an oxidative synthesizing agent containing a promoting amount of alkaline earth metal and/or compounds thereof.

Commonly-assigned U.S. patent application Ser. Nos. 06/600,665; 06/600,918 06/600,917; 06/600,730 and 06/600,969 disclose processes for the conversion of methane to higher hydrocarbons which comprises contacting methane with solids comprising the oxides of Pr, Tb, Ce, Fe and Ru, the oxides being reduced by contact with methane at temperatures within the range of about 500° to about 1000° C. The entire contents of these applications are incorporated herein by reference.

The reaction products of such processes are mainly ethylene, ethane, other light hydrocarbons, carbon oxides, coke and water.

SUMMARY OF THE INVENTION

A method is disclosed for converting methane to higher hydrocarbon products which comprises contacting a gas comprising methane in a methane converson zone with a solid comprising at least one reducible oxide of at least one metal which oxide(s) when contacted with methane at temperatures selected within the range of about 500° to 1000° C. are reduced and produce higher hydrocarbon products and water, the improvement which comprises recycling $C_2+$ alkanes recovered during subsequent processing of the effluent produced by the contacting to the methane conversion zone.

DETAILED DESCRIPTION OF THE INVENTION

In addition to methane the feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof. Alakali and alkaline earth metals and compounds have been found to improve the hydrocarbon product selectivity of these agents. The further incorporation of phosphorus into agents promoted by alkali or alkaline earth components enhances catalyst stability.

Reducible oxides of cerium, praseodymium, and terbium have also been found to be effective for the conversion of methane to higher hydrocarbons, particularly when the rare earth component is associated with an alkali and/or an alkaline earth component. Reducible oxides of iron and ruthenium are also effective for the conversion of methane to higher hydrocarbons, particularly when associated with an alkali and/or an alkaline earth component.

The metal components may be associated with other support materials such as silica, magnesia, alumina, titania, zirconia and the like and combinations thereof. When employing agents containing rare earth components—oxides of Ce, Pr and Tb—or such components as Fe and Ru, the rare earth oxides or oxides of Fe or Ru preferably serve as supports.

Reducible oxides of manganese have been found to be particularly desirable for methane conversion, especially when associated with an alkali metal (preferably sodium). Especially preferred agents comprise silica- and/ or magnesia- supported agents containing oxides of manganese and sodium.

The solid contacted with methane in the first step of the present invention can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkali or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solids calcined, preferably in air, at a temperature within the range of about 300° to 1200° C. Particular calcination temperatures will vary depending upon the particular metal compound or compounds employed.

Regardless of how the components of the agent are combined, the composite will be dried and calcined at elevated temperatures prior to use of the process of this invention.

Preferably, methane is contacted with the agent in the substantial absence of catalytically effective nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the first step of this invention relative to such contacting in the absence of such metals and compounds thereof.

Operating temperatures for the methane contact step are preferably within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

Methane conversion may be accomplished in a single reactor apparatus containing a fixed bed of solids with intermittent or pulsed flow of a first gas comprising methane and a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising at least one reducible oxide of at least one metal to form higher hydrocarbon products, co-product water, and reduced metal oxide; (b) removing particles comprising reduced metal oxide from the first zone and contacting the reduced particles in a second zone with an oxygen-containing gas to form particles comprising a reducible metal oxide; and (c) returning the particles produced in the second zone to the first zone. The steps are preferably repeated at least periodically, and more preferably the steps are continuous. In the more preferred embodiment solids are continuously circulated between at least one methane-contact zone and at least one oxygen-contact zone.

Particles comprising a reducible metal oxide which are contacted with methane may be maintained as fluidized, ebullating, or entrained beds of solids. Preferably methane is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In the more preferred embodiment of the present invention, methane feedstock and particles comprising a promoted oxidative synthesizing agent are continuously introduced into a methane contact zone maintained at synthesizing conditions. Synthesizing conditions include the temperatures and pressures described above. Gaseous reaction products from the methane contact zone (separated from entrained solids) may be further processed—e.g., they may be passed through a fractionating system wherein the desired hydrocarbon products are separated from unconverted methane and combustion products. Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative synthesizing agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

The effluent produced by the methane conversion step of the method of this invention comprises unconverted methane and higher hydrocarbons as well as carbon oxides and water. The effluent is referred to herein as "redox effluent." It is within the scope of the present invention to recover at least a portion of the $C_{2+}$ alkanes present in the redox effluent for recycle to the methane contact zone.

The redox effluent also comprises $C_{2+}$ olefins which may be oligomerized to form higher hydrocarbon products. The oligomerization techniques which may be employed have been broadly described in concurrently filed U.S. patent application Ser. No. 06/600,657, the entire content of which is incorporated herein by reference. The redox effluent will typically comprise a mixture of olefins containing a major amount of ethylene. One presently preferred technique for oligomerizing such a mixture is disclosed in concurrently filed U.S. patent application Ser. No. 06/604,785, the entire content of which are incorporated herein by reference.

In addition to alkanes present in the redox effluent, some alkane formation will occur while oligomerizing $C_{2+}$ olefins. Accordingly, $C_{2+}$ alkanes may be recovered directly from the redox effluent and/or $C_{2+}$ alkanes may be recovered from the effluent produced by subsequent oligomerization of all or a portion of the redox effluent. Moreover, if the redox effluent is oligomerized in a multi-step process, $C_{2+}$ alkanes may be recovered from intermediate process streams. Also, as will be apparent to one skilled in the art, various alkane fractions may be recovered for recycle to a methane-contact zone. For example, separate recovery of methane/ethane and propane/butane fractions may be desirable, e.g., when the redox effluent comprises ethylene and $C_{3+}$ olefins, and the ethylene is first converted to additional $C_{3+}$ olefins which are then oligomerized to produce normally liquid hydrocarbon products. See U.S. patent application Ser. No. 06/604,785.

Separation of various fractions containing $C_{2+}$ alkanes from various process streams may thus occur in a process comprising methane conversion to olefins and olefin oligomerization to higher hydrocarbons. Any such separation and recycle to the methane contact zone is within the scope of the present invention.

A principle advantage of this invention is the increased yields of higher hydrocarbons obtained when converting methane to normally liquid hydrocarbons. $C_{2+}$ alkanes are easily converted in the methane contact zone to products comprising $C_{2+}$ olefins, thereby enhancing the higher hydrocarbon yield of the methane contact zone.

What is claimed is:

1. In a method for converting methane to higher hydrocarbon products which comprises contacting a gas comprising methane in a methane conversion zone with a solid comprising at least one reducible oxide of at least one metal which oxide(s) when contacted with methane at temperatures selected within the range of about 500° to 1000° C. are reduced and produce higher hydrocarbon products and water, the improvement which comprises recycling $C_2+$ alkanes recovered during subsequent processing of the effluent produced by said contacting to said methane conversion zone.

2. The method of claim 1 wherein said reducible metal oxide is selected from the group consisting of oxides of Mn, Sn, In, Ge, Sb, Pb, Bi and mixtures thereof.

3. The method of claim 1 wherein said reducible metal oxide is an oxide of manganese.

4. The method of claim 3 wherein the gas comprising methane is contacted with a solid comprising said oxide of manganese and at least one alkali metal or compound thereof.

5. The method of claim 3 wherein the gas comprising methane is contacted with a solid comprising said oxide of manganese and sodium or compounds thereof.

6. The method of claim 4 wherein said manganese component and said alkali metal component are associated with a support material.

7. The method of claim 6 wherein said support is silica.

8. The method of claim 6 wherein said support is magnesia.